(12) United States Patent  (10) Patent No.: US 8,267,958 B2
Braun  (45) Date of Patent: *Sep. 18, 2012

(54) SURGICAL INSTRUMENT COMPRISING AN INSTRUMENT HANDLE AND ZERO POINT ADJUSTMENT

(75) Inventor: Marcus Braun, Stuttgart-Vaihingen (DE)

(73) Assignee: Tuebingen Scientific Surgical Product GmbH, Tuebingen (DE)

( * ) Notice: Subject to any disclaimer, the term of this patent is extended or adjusted under 35 U.S.C. 154(b) by 271 days.

This patent is subject to a terminal disclaimer.

(21) Appl. No.: 12/370,187

(22) Filed: Feb. 12, 2009

(65) Prior Publication Data

US 2009/0192521 A1  Jul. 30, 2009

Related U.S. Application Data

(62) Division of application No. 10/853,713, filed on May 26, 2004, now Pat. No. 7,549,998.

(30) Foreign Application Priority Data

Jun. 2, 2003 (DE) .................................. 103 24 844

(51) Int. Cl.
*A61B 17/28* (2006.01)
(52) U.S. Cl. ..................................................... 606/205
(58) Field of Classification Search .................. 606/170, 606/171, 205–208, 211, 51, 52; 600/104, 600/142, 225, 218
See application file for complete search history.

(56) References Cited

U.S. PATENT DOCUMENTS

| | | |
|---|---|---|
| 3,847,154 A | 11/1974 | Nordin |
| 4,950,273 A | 8/1990 | Briggs |
| 5,002,553 A | 3/1991 | Shiber |
| 5,147,357 A | 9/1992 | Rose et al. |
| 5,174,300 A | 12/1992 | Bales et al. |
| 5,549,637 A | 8/1996 | Crainich |
| 5,702,408 A | 12/1997 | Wales et al. |
| 5,776,155 A | 7/1998 | Beaupre et al. |
| 5,797,956 A | 8/1998 | Furnish et al. |
| 5,827,323 A | 10/1998 | Klieman et al. |
| 5,972,012 A | 10/1999 | Ream et al. |
| 6,913,613 B2 | 7/2005 | Schwarz et al. |
| 2001/0041911 A1 | 11/2001 | Dittrich et al. |
| 2002/0055758 A1 | 5/2002 | Sasaki |
| 2003/0144681 A1 | 7/2003 | Sample |

FOREIGN PATENT DOCUMENTS

| | | |
|---|---|---|
| DE | 100 36 108 A1 | 7/2000 |
| GB | 2189735 A | 11/1987 |

*Primary Examiner* — Elizabeth Houston
(74) *Attorney, Agent, or Firm* — Arent Fox LLP

(57) ABSTRACT

The invention relates to a surgical instrument comprising an instrument handle linked to a proximal end portion of a tube shaft to the distal end portion of which an instrument head is linked so as to be bendable, in which instrument head an effector including at least one pivotal engaging element is rotatably supported. The instrument handle has a number of manipulators and/or operating mechanisms for operating the instrument head and/or the effector via gear trains. According to the invention, a clutch which permits a zero point adjustment individual at least over a predetermined pivoting range of the instrument handle is interposed in the gear train effecting the bending motion of the instrument head. The zero point is defined as a relative position of the instrument handle with respect to the tube shaft in which the instrument head adopts a predetermined bending position with respect to the tube shaft.

9 Claims, 6 Drawing Sheets

SURGICAL INSTRUMENT COMPRISING AN INSTRUMENT HANDLE AND ZERO POINT ADJUSTMENT

CROSS-REFERENCE TO RELATED APPLICATION

Figure 1:
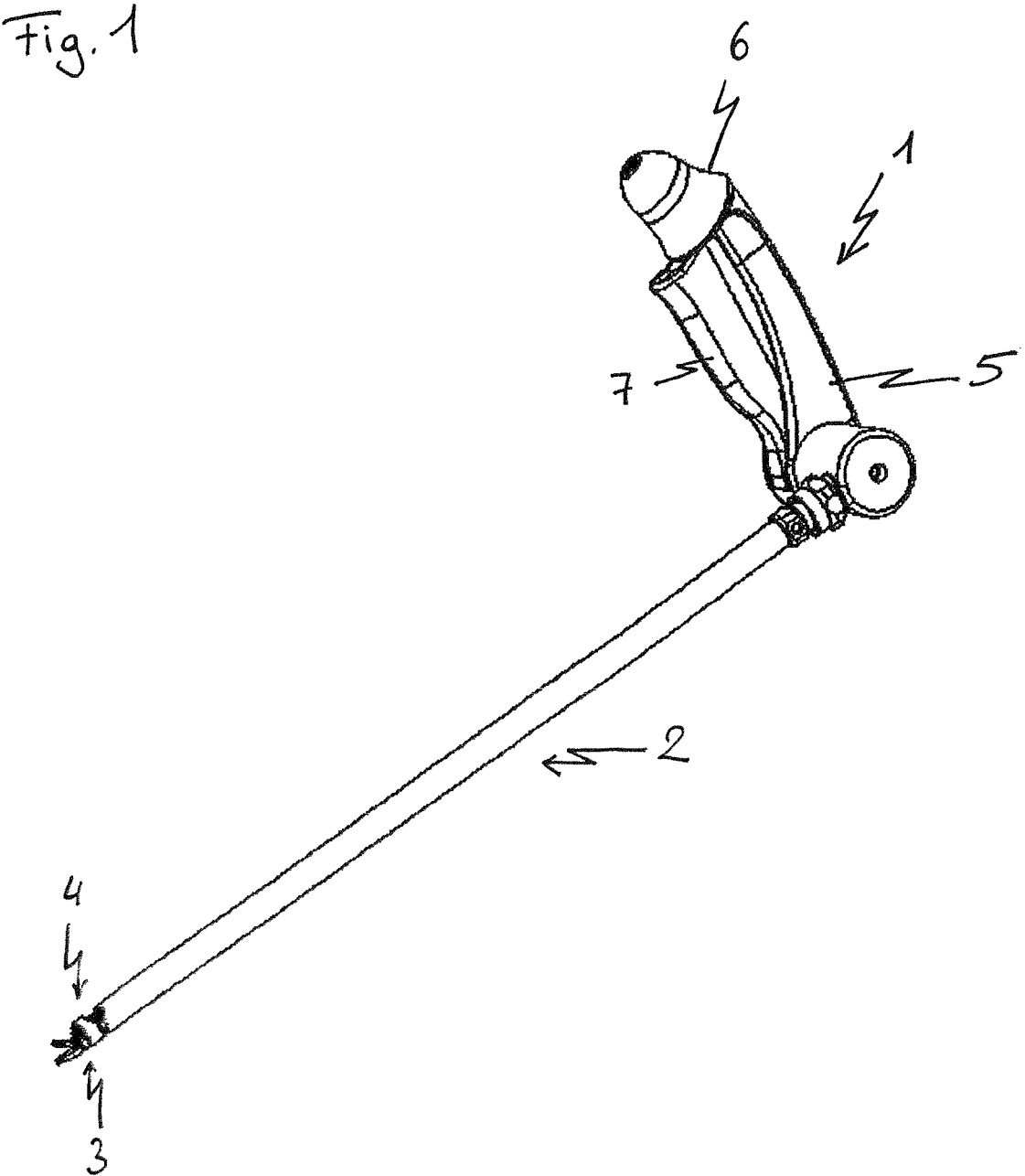

This application is a divisional of U.S. application Ser. No. 10/853,713, filed May 26, 2004, now pending, which claims priority to German Application No. 10324844.7, filed Jun. 2, 2003, the disclosure of the prior applications is hereby incorporated in its entirety by reference.

The present invention relates to a surgical instrument for minimally invasive surgery in accordance with the preamble of claim 1.

From DE 100 36 108 a surgical instrument of this generic type is known. It substantially comprises a tube shaft at the one proximal end of which an instrument handle is arranged by which an instrument head disposed at the opposed distal end of the tube shaft is operable through gear trains. The instrument head can be pivoted and/or inclined with respect to the tube shaft and moreover holds an effector rotatably supported in the instrument head in the form of forceps or tongs whose one jaw is pivoted to the effector and is likewise operable by means of the instrument handle.

In more concrete terms, the gear trains enable at least a first movement of the instrument handle, according to this prior art to be triggered by the hand rotation of an operator, to be transformed into a rotation of the effector at a predetermined transmission ratio with respect to this operating movement. Thus it is possible to rotate the effector despite the relatively restricted motion capacity of a human hand by up to 300°, for instance, and in this way to realize complex motions without having to change the grip at the handle. Moreover a second motion of the instrument handle, for instance bending thereof with respect to the tube shaft, is converted into an inclination motion of the instrument head.

The gear trains provided inside the instrument handle and the tube shaft are designed such that most largely decoupled operation of each individual movement of the instrument head and the effector is permitted. However, such gears are necessarily extremely complex and consequently also require sufficient assembly space. Moreover a complete declutch of the individual movements is not fully ensured.

It has also turned out that, especially in the case of a hand rotation for turning the effector supported in the instrument head, the natural structure of the hand and the motions resulting therefrom, i.e. irrespective of whether or not the gear trains of the surgical instrument are in fact completely decoupled, at the same time cause a slight bending of the instrument tip and, moreover, a tilting of the entire instrument shaft, which considerably impedes the handling of the instrument.

In view of this prior art, it is the object of the present invention to provide a surgical instrument of this generic type in which motions of an instrument head as well as of an effector can be performed largely independently of the natural conditions of a natural hand structure, decoupled from each other via an instrument handle.

This object is achieved by a surgical instrument comprising the features according to claim 1.

In principle, the individual degrees of freedom as well as the motion ranges of a human hand are predetermined in a restricted range due to its structure and individually deviate only slightly from each other. The use of a generic surgical instrument frequently cannot take restrictions of the human hand in terms of kinematics into consideration, however. In other words, an optimum use of the surgical instrument requires a position of the hand or of the surgeon which might be unnatural. This entails the fact that such positions cannot be maintained for a long time or only with great expenditure of force so that moreover in such positions it is very difficult to work exactly with the surgical instrument.

Based on these considerations, the core of the invention now consists in pivotally connecting the instrument handle to the tube shaft via a clutch or, more precisely, in interposing a clutch into the gear train for transmitting a swivel motion of the instrument handle to the instrument head for bending the same, which clutch permits an individual zero point adjustment at least in a predetermined range, wherein the zero point is a relative position of the instrument handle with respect to the tube shaft in which the instrument head adopts a predetermined bending position, preferably the maximum or minimum bending position (stop position) with respect to the tube shaft.

By this technical measure the instrument handle and/or the relative position thereof with respect to the tube shaft can be aligned in response to the application position of the instrument so that the surgeon is substantially able to grasp and operate the instrument handle substantially within the natural motion range of his hand. Thus, the surgical instrument according to the invention makes it possible to do precise work without getting tired.

It is advantageous to design the clutch to be automatically disconnecting. I.e. such a clutch is automatically disconnected when a predetermined torque is exceeded and/or transmits only this predetermined torque and above that it begins to slip.

It is an advantageous possibility of a constructional configuration of an automatically disconnecting clutch to design a slipping clutch which basically provides two torque transmission elements forced against each other which slip off each other from a defined torque. Specifically, the torque transmission elements are biased against each other so that they are adapted to transmit a torque within the scope of a conventional use of the instrument by corresponding frictional contact, which torque is exceeded by further pivoting of the instrument head and thus the relative position of both torque transmission elements is varied, however, in case that the instrument head is in its maximum or minimum bending stop position.

As an alternative, it is also possible, of course, to manually disengage two torque transmission elements of the clutch for a zero point adjustment, wherein in this case it must be ensured, however, that the predetermined position of the instrument head is observed for a well-directed adjustment of the zero point.

As a further alternative for an automatically disconnecting clutch, also an engaging element, for instance in the form of at least one driving tooth or at least one ball, may be provided which is supported on one of the torque transmission elements and is biased against the other torque transmission element and engages in a recess or undercut. Hereby a positive fit connection is provided which is released upon exceeding a torque defined by the spring bias and the two torque transmission elements are twisting relative to each other.

Another advantageous configuration of the invention provides to arrange the clutch in the area of the link point between the instrument handle and the tube shaft. This has the advantage that when dimensioning the clutch there are fewer spatial restrictions, because this section of the instrument is basically always disposed outside the body to be operated and moreover for safe handling this area is designed to be large anyway in accordance with the dimensions of a human hand.

Further advantageous configurations of the invention are the subject matter of the subclaims.

Hereinafter the invention will be shown in detail by way of a preferred embodiment with reference to the accompanying drawings.

Figure 2:
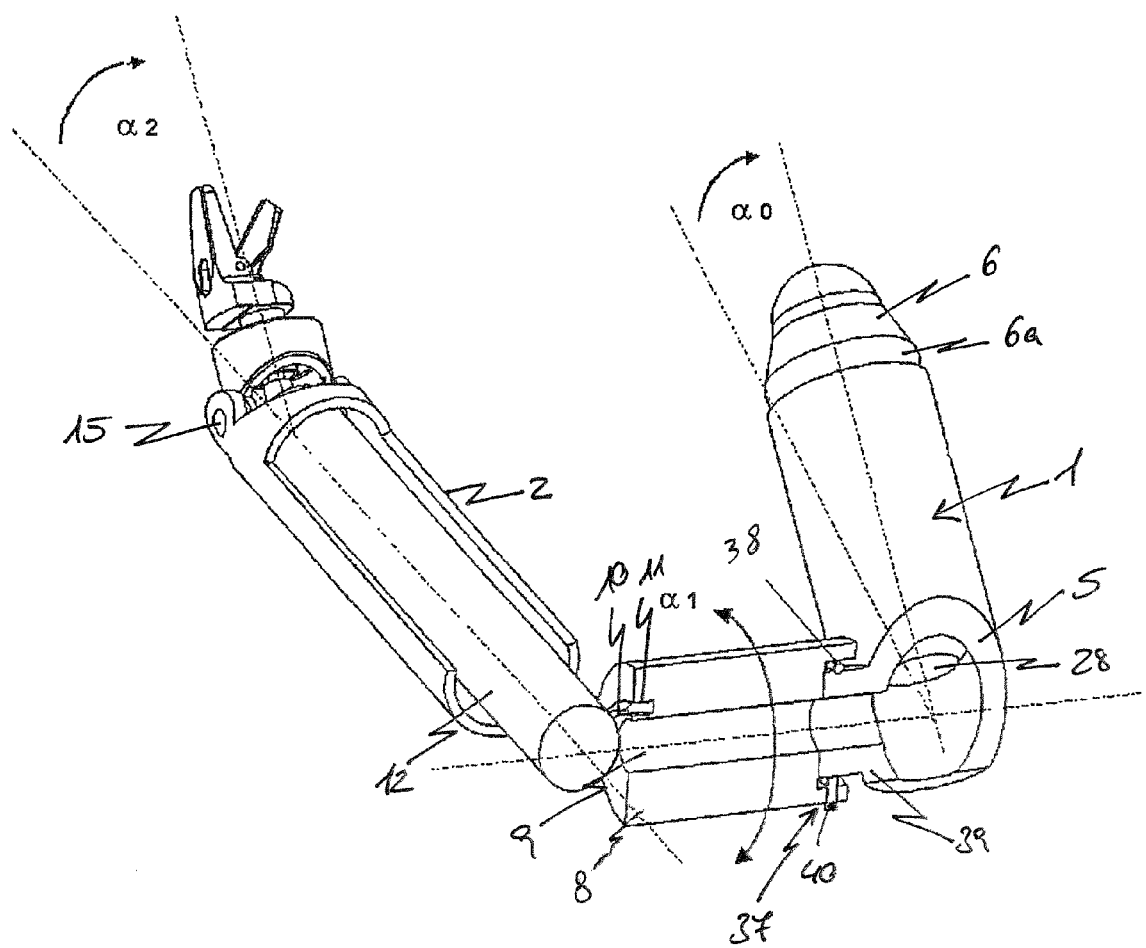
Figure 3:
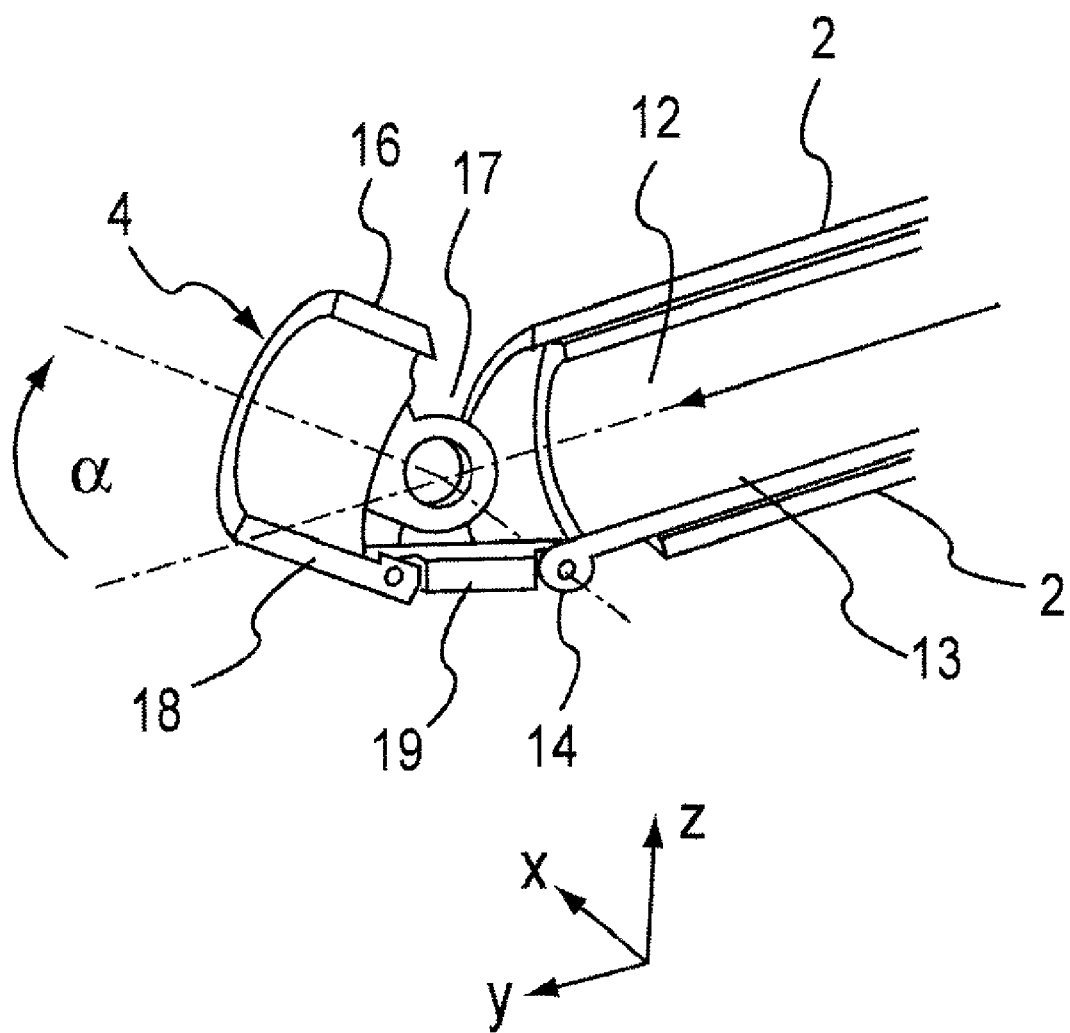
Figure 4:
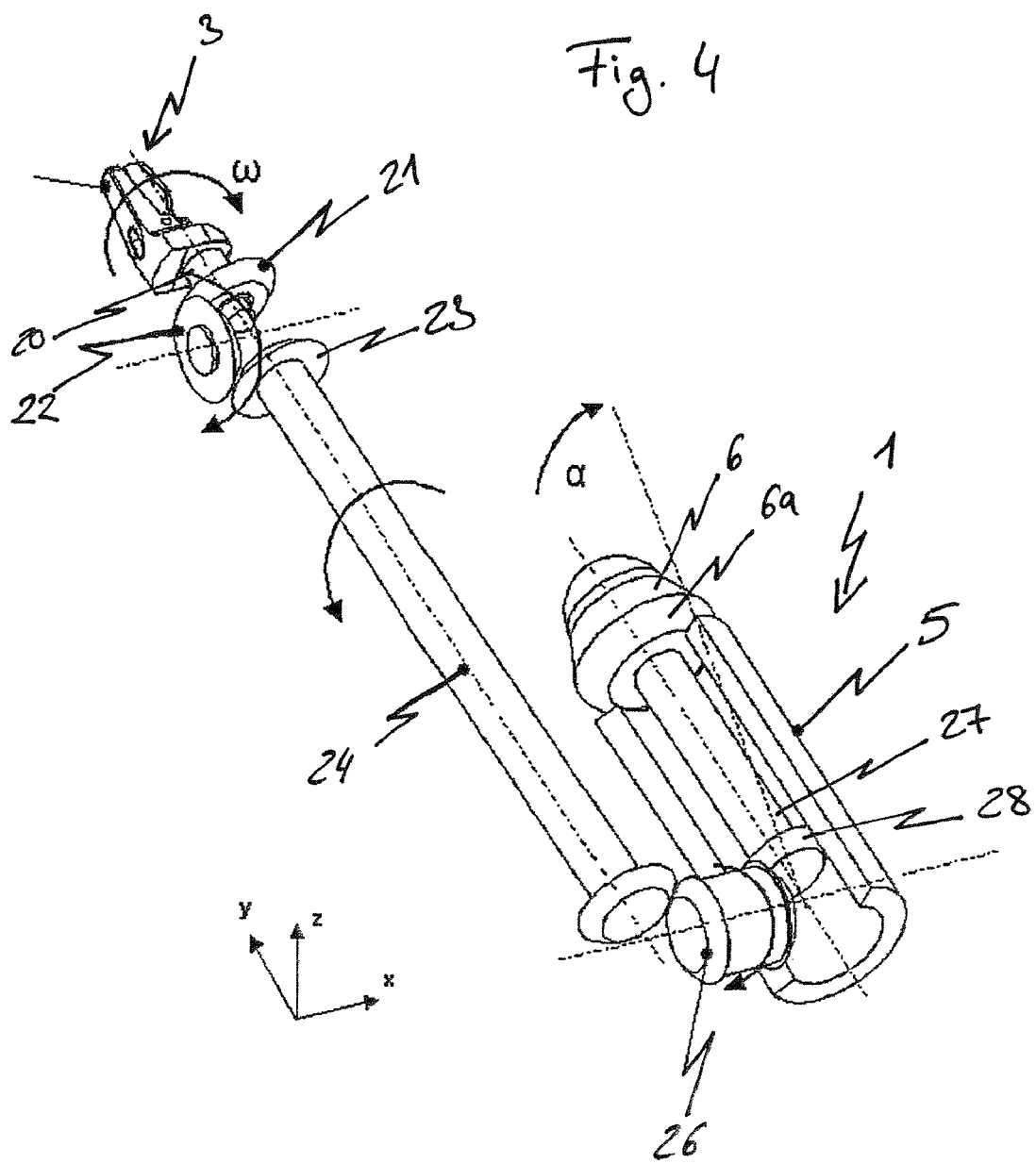
Figure 5:
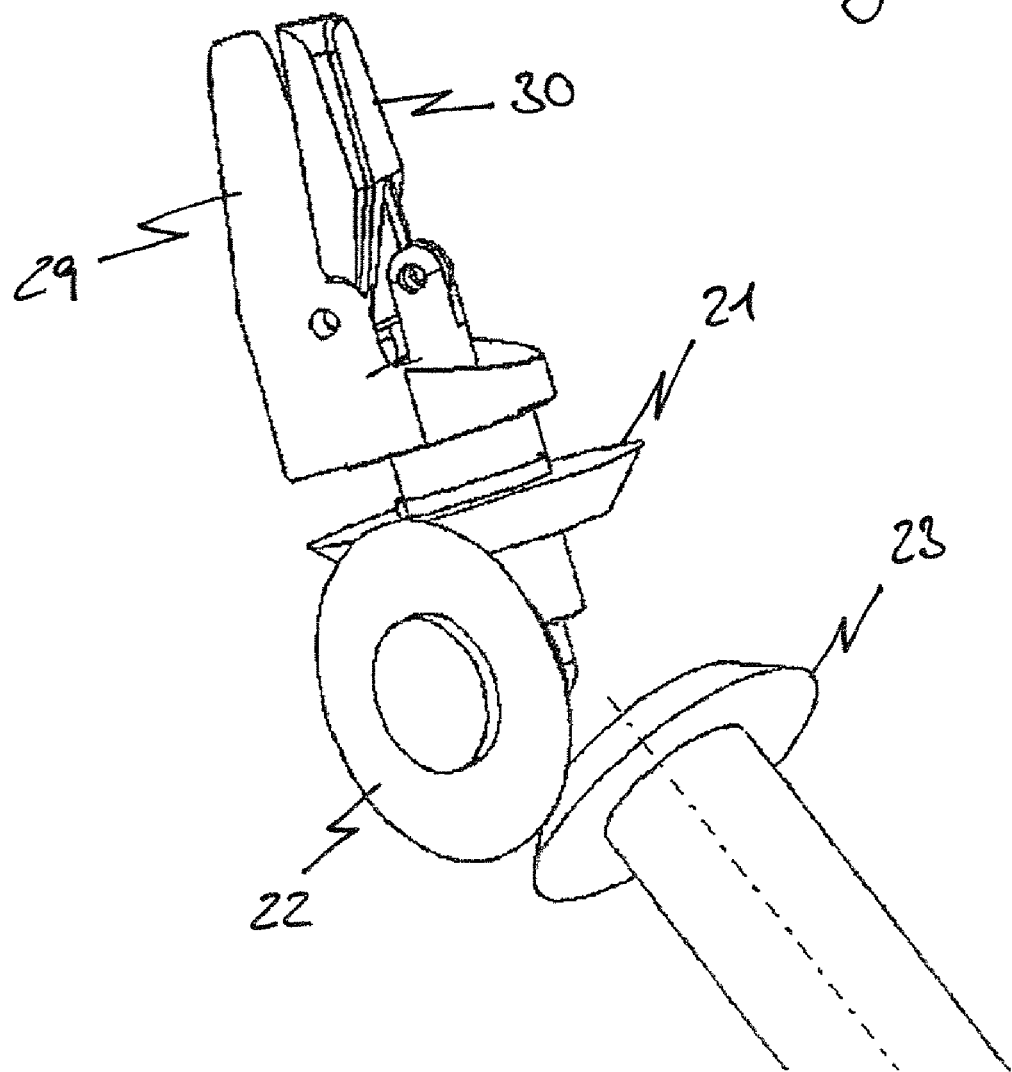
Figures 6A, 6B, 6C:
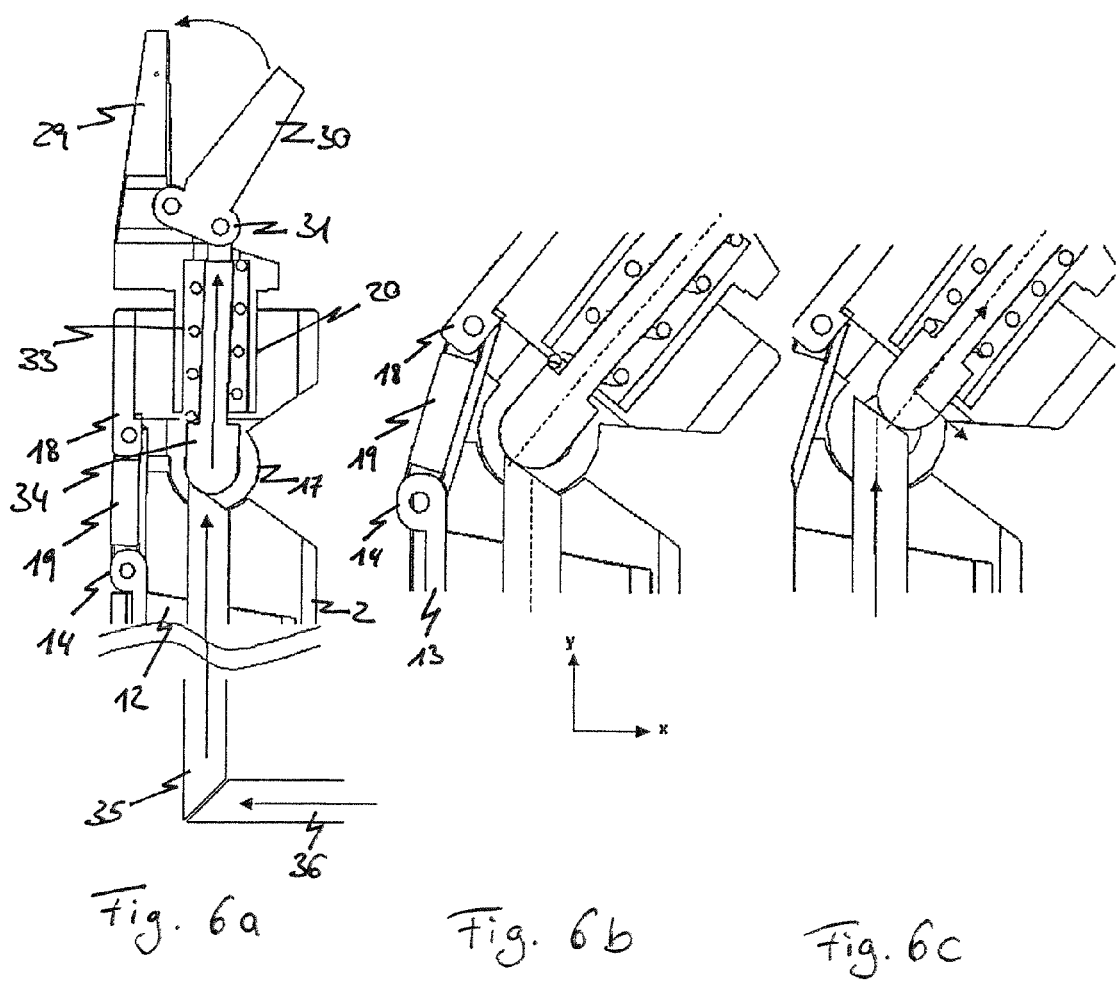

FIG. 1 shows a perspective view of a surgical instrument according to a preferred embodiment of the invention, FIG. 2 shows a first gear train for pivoting an instrument head by means of an instrument handle as well as especially a zero point adjusting device in the linking area of the instrument handle, FIG. 3 shows a partial section of the first gear train in the pivoting area of the instrument head, FIG. 4 shows a second gear train for a rotation of the instrument head by means of the instrument handle, FIG. 5 shows a partial section of the second gear train in the pivoting area of the instrument head, and FIGS. 6a-6c show sectional views of a third gear train in the pivoting area of the instrument head for actuating forceps supported on the instrument head.

In FIG. 1 a complete surgical instrument according to a preferred embodiment of the invention is shown in a perspective view. The surgical instrument according to the invention consequently includes a multi-functional instrument handle 1 arranged at a proximal end or end portion of a tube shaft 2 preferably made of stainless steel, a steel alloy or a plastics material as well as an instrument head 4 equipped or adapted to be equipped with an effector 3 which is provided at the other, distal end of the tube shaft 2.

In general, the instrument head 4 is supported on the respective end of the tube shaft so that it can be pivoted or bent with respect to the tube shaft 2, whereas the effector 3 can be rotated in each bending position of the instrument head 4 about the longitudinal axis thereof, the two above-mentioned motions being adapted to be performed by means of the instrument handle 1. To this effect, a number of manipulators and/or operating mechanisms are provided at the instrument handle 1 which are operatively connected via appropriate gear trains provided inside the instrument handle 1 and the tube shaft 2 to the instrument head 4 and the effector 3, respectively, so as to be able to perform the individual movements of the instrument head 4 and the effector 3 independently of each other, i.e. in a decoupled manner.

Specifically, the instrument handle 1 consists of an ergonomically shaped handle member 5 which is mounted in a pivoting and inclinable manner to the tube shaft 2 and on which a first manipulator 6, in the present case preferably in the form of a turning knob, and a second manipulator 7, in the present case preferably in the form of a handle lever, are supported. Thus, the instrument handle 1 according to the preferred embodiment of the present invention comprises a total of three operating mechanisms for three independent movements of the and [sic] on the instrument head 4, respectively. It is explicitly emphasized in this context that the instrument handle 1 may also have fewer operation possibilities, for instance only one operating mechanism, respectively, for pivoting the instrument head 4 and rotating the effector 3.

The exterior structure of the instrument handle 1, especially with respect to the operating mechanism for pivoting and bending the instrument head 4 and with respect to the corresponding bending gear train is shown in FIGS. 2 and 3.

The handle member 5 schematically shown in FIG. 2 is pivotally connected to the tube shaft 2 via a crank member 8 which is connected to the handle member 5 through a clutch 7 further described hereinafter and has the form of a rotary shaft or rotary disk. The rotary shaft 8 is preferably aligned so as to be perpendicular to the tube shaft 2 as well as to the handle member 5 and spaces the handle member 5 from the tube shaft 2 such that the latter can be pivoted substantially in parallel to the tube shaft 2 past the same.

At the handle member 5 itself, a kind of tube or sleeve-shaped connecting base 39 is fastened to the proximal end portion thereof which extends substantially perpendicularly, i.e. in a radial direction away from the handle member 5. The tubular connecting base 39 includes at its free end an outer sliding face (not shown in detail) onto which an open lock washer 38 is placed under stress.

The rotary shaft 8 is rotatably placed on the connecting base 39 at its end portion facing the handle member 5. To this end, the rotary shaft 8 is bored open at the inside over a predetermined axial length to an inner diameter which is so much larger than the outer diameter of the connecting base 39 that at least a clearance fit is provided between the same and the rotary shaft 8. Hereby a circumferential surface having a predetermined radius is formed at the bored open inner wall of the rotary shaft 8, with a radially extending pin 40 which is inserted through a radial through bore from the sheath side of the rotary shaft to the inside projecting therefrom.

When assembling the rotary shaft 8 it is attached to the connecting base 39 until the lock washer 38 is positioned on or at the inner circumferential sliding face of the rotary shaft 8. The pin 40 projects into the radial gap formed by the open lock washer 38 and thus makes a positive fit connection between the rotary shaft 8 and the lock washer 38 which, in turn, forms a frictional engagement with the connecting base 39. It is explicitly pointed out in this context that the foregoing clutch may also be designed in an inverse manner in terms of kinematics, i.e. the lock washer 38 may be provided in the rotary shaft 8 by frictional engagement and may enter into a positive fit connection with a pin which is inserted in the connecting piece.

If the instrument handle 1 is now pivoted about its pivot axis (corresponding to the central axis of the rotary shaft 8), the pivoting motion is transmitted via the lock washer 38 seated on the circumferential sliding face of the connecting base 39 or on the rotary shaft 8 by frictional engagement to the pin 40 projecting into the lock washer gap and thus to the rotary shaft 8 or the connecting piece 39 which consequently rotates integrally with the instrument handle 1. The maximum torque to be transmitted is defined by the biasing force by which the lock washer 38 is placed onto the circumferential sliding face. As soon as this torque has been exceeded, the lock washer 38 starts sliding on the circumferential sliding face, whereby the relative position of rotation between the instrument handle 1 and the rotary shaft 8 is varying.

In this context, it is referred to the fact that the lock washer 38 of course may also be caught in respective circumferential guides, for instance in the form of inner and/or outer grooves provided at the rotary shaft 8 and/or the connecting base 39 so as to have an axial guiding.

The rotary shaft 8 forming a central through passage 9 for accommodating gear members, which will be described hereinafter, is designed on its one front facing the tube shaft 2 to include a crank guide 10 in the form of a cam-shaped groove in which a driving pin 11 engages which is fastened to an axially movable pushing tube 12 supported in a tube shaft 2. The groove 10 is formed such that during a motion of rotation of the rotary shaft 8 by appropriately pivoting the handle member 1 the driving pin 11 slides along the groove 10 and, in so doing, performs a forced compensating motion in the longitudinal direction of the tube shaft 2 which is transmitted to the pushing tube 12 and, depending on the direction of rotation of the rotary shaft 8, results in a reciprocating movement of the pushing tube 12 inside the tube shaft 2.

The above-described structure is finally held together by a hub in the form of a hub bolt (not shown in detail) which is fixed to the tube shaft and penetrates the rotary shaft 8 as well as the handle member 5 in the pivot axis thereof and is fixed by a nut likewise not shown in detail.

The distal end portion of the pushing tube 12 opposed to the crank member 8 is designed to include a longitudinal extending mounting link 13 projecting from the distal end of the pushing tube 12 and forming a hinge and/or hinge eyes 14 at its free end portion. Moreover the front of the tube shaft 2 is beveled at its distal end portion at an angle of preferably 45° and is formed to include lateral link eyes 15 to which the instrument head 4 is pivotally linked via pivot pins. The same likewise consists of a tube member 16 whose one front at which control eyes 17 are formed for the connection to the tube shaft 2 and the link eyes 15 thereof is equally beveled at an angle of preferably 45°, namely such that after linking the instrument head 4 to the tube shaft 2 the two aforementioned bevels are complementary and enable the tube member 16 to bend with respect to the tube shaft 2 by about 90°, preferably 70°.

Moreover a hinge and/or hinge eyes 18 is/are formed at the beveled front of the tube member 16. To the hinge eyes 14; 18 provided on the pushing tube side and on the tube member side a rocking lever 19 is hinged which is consequently offset radially outwardly with respect to the pivot axis of the instrument head 4 and transmits an axial translational motion of the pushing tube 12 to the tube member 16, whereby the latter is pivoted about its pivot axis.

Hereinafter, by way of the FIGS. 4 and 5 the operating mechanism for a rotation of the effector 3 supported in the instrument head 4 as well as the corresponding rotation gear train are described.

As one can further take from FIG. 2, the above-mentioned tube member 16 of the instrument head 4 simultaneously constitutes a casing and/or a receptacle for the effector 3. Irrespective of which type of effector this is, i.e. irrespective of whether for instance a needle holder, tongs, forceps or scissors are used as effector, the latter has a preferably hollow rotational axis 20 which is rotatably inserted in the tube member 16 of the instrument head 4 and is secured against an axial movement. The length of this rotational axis 20 is selected so that it ends approximately in the area of the pivot axis of the instrument head 4 and is provided at its free end projecting toward this pivot axis with an output spur gear 21 which is mounted on the rotational axis 20 of the effector 3 in a torque-proof manner. Especially in FIG. 2 the pivot axis of the instrument head 4 is shown by a broken line through the eyes 15.

As one can further take from FIG. 5, on the pivot axis of the instrument head 4 a torque transmission spur gear 22 is provided which is pivoted to one of the two pivoting pins of the instrument head 4 not shown in detail, which form the pivot axis shown in an idealized way, and is in mesh with the output spur gear 21. The torque transmission spur gear 22, in turn, is in mesh with a drive spur gear 23 that is mounted in a torque-proof manner on a drive shaft 24 rotatably guided inside the pushing tube 12 (not shown in FIGS. 4 and 5), as it is especially shown in FIG. 4. At the end of the drive shaft 24 opposing the drive spur gear 23 a further torque initiating spur gear 25 is arranged in a torque-proof manner, according to FIG. 4, which is in mesh with a long-face pinion 26 supported in the central through passage 9 formed inside the crank member 8.

The crank member 8 is not shown in FIG. 4.

Ultimately, the long-face pinion 26 is in mesh with an actuating shaft 27 and a spur gear 28 attached thereto inside the handle member 5, the actuating shaft being fixedly connected to the one manipulator, the turning knob 6 in the present case.

As one can take especially from FIG. 4, the turning knob 6 forms the distal tip or the outer end of the instrument handle 1. It is fixedly connected to the actuating shaft 27 extending substantially along the longitudinal axis of the handle member 5. The turning knob 6 includes a rear edge portion facing the handle member 5 schematically shown as sleeve in FIG. 4 which edge portion is sliding adjacent to the handle member 5 and thus seals the handle member 5 at its distal end.

When actuating the turning knob 6 the motion of rotation thereof is transmitted via the actuating shaft 27 inside the handle member 5, the long-face pinion 26, the connected driving shaft 24 inside the pushing tube 12 as well as the transmission spur gear 22 to the effector 3 and the latter is rotated. The turning knob 6 is advantageously operated by the fingers, especially by the thumb and the index, of the operator's hand, while the handle member 5 is held in hand. Thus it is possible to generate any rotation at the effector 3 without the operator having to change his grip at the handle member 5. The fingers of a human hand are adapted to work in a fine-motor way and also the finger tips are provided with a plurality of nerve endings permitting a distinct tactile feeling. Accordingly, motions which require high accuracy should be performed by the fingers. It has turned out that the rotation of the effector 3 is such a motion and therefore, according to the invention, is triggered by the turning knob 6 without a motion being transmitted to the tube shaft 2 by advantageously turning the knob 6 for a rotation of the effector 3. Rather, the operator's hand can be maintained steady.

It is furthermore pointed out in this context that the driving shaft 24 and the pushing tube 12 are supported to be movable in axial direction relative to each other. I.e., rotation of the crank member 8 triggered by pivoting the instrument handle 1 does cause a translational motion of the pushing tube 12, yet, at the same time, the driving shaft 24 is held in position, i.e. in mesh with the long-face pinion 26, thereby the pushing tube 12 performing an axial movement relative to the tube shaft 2 as well as to the driving shaft 24.

Finally hereinafter the operating mechanism for the effector 3, i.e. the functions thereof and the corresponding effector gear train are described by way of the FIGS. 5 and 6a-6c.

In accordance with FIG. 5, in the present embodiment of the invention the effector 3 is designed as tongs having one fixed jaw 29 and one movable, i.e. pivotal jaw 30. The fixed jaw 29 forms a unit together with the rotary shaft 20 of the effector 3 and is preferably designed integrally with the rotary shaft 20, whereas the movable jaw 30 is linked to the fixed jaw 29 to be pivotal at one end.

The movable jaw 30 forms a linking point 31 for a push pin 32 which is supported inside the rotary shaft 20 so as to be relatively movable so that by axial displacement thereof a pivotal motion of the movable jaw 30 with a maximum possible transmission is caused. As particularly shown in FIG. 6a-6c, the push pin 32 is axially biased by a spring 33 in the opening direction of the tongs enclosing the push pin 32 inside the rotary shaft 20. For this purpose, the push pin 32 forms a shaft protrusion on which the biasing spring 33 is supported at its one end. The other end of the biasing spring 33 is supported against the fixed jaw 29 of the tongs. An end piece 34 of the push pin 32 projecting from the rotary shaft 20 in the direction of the pivot axis of the instrument head 4 has a ball-shaped head, the radius of the ball-shaped head 34 in the present case preferably being about 2.5 mm.

The aforementioned drive shaft 24 for rotationally driving the effector 3 supported in the instrument head 4 is provided with a substantially continuous axial bore (not shown in detail). In this axial bore, a pushing bar 35 is guided to be axially movable as well as rotatably guided relative to the drive shaft 24, the front face of the pushing bar facing the pushing pin 32 being chamfered corresponding to the chamfers of the distal front faces provided at the tube shaft side and the pushing tube side, i.e. preferably 45° in the same direction. The pushing pin 32 is biased against this chamfered front face of the pushing bar 35 by the spring 33 and abuts against the same. The contact face between the pushing bar 35 and the pushing pin 32 is substantially punctiform due to the aforedescribed ball-shaped head of the pin 32, namely independently of the degree of bending of the instrument head 4 and independently of the position of rotation of the effector 3.

As can be seen from FIG. 6a, the pushing pin 32 as well as the pushing bar 35 are aligned axially with respect to each other in case that the bending of the instrument head 4 with respect to the tube shaft 2 is substantially 0°. Moreover, in this position of the instrument head 4, the pushing pin 32 is positioned such that the center of the ball-shaped head 34 of the pushing pin 32 is located approximately in the pivot axis of the instrument head 4.

At its proximal end, the pushing bar 35 is connected via a gear mechanism 36, not shown in detail, to the actuating lever 7 which is pivoted to the handle member 5, as already briefly explained at the beginning of this description.

The functioning of the surgical instrument according to the invention will be described hereinafter in detail.

Rotation of the effector 3 supported in the instrument head 4 is effected by actuating the turning knob 6 supported at one end of the handle member 5, wherein, as explained already in the foregoing, the turning knob 6 can be turned about its axis of rotation so far that a rotation of approx. 360° is realized at the effector 3 without the grip at the handle member 5 necessarily having to be changed. This motion of rotation is transmitted via the actuating shaft 27 to the long-face pinion 26 which, in its turn, transmits its rotation to the drive shaft 24 extending inside the pushing tube 12. The motion of rotation of the drive shaft 24 causes a rotation of the transmission spur gear 22 which quasi bridges the pivot axis of the instrument head 4 and thus triggers a motion of rotation of the effector 3 inside the tube member 16 of the instrument head 4 about the tube member axis.

According to the present embodiment, the entire handle member 5 has to be pivoted about the longitudinal axis of the crank member and the rotary shaft, respectively, to effect a bending, i.e. a pivoting movement of the instrument head 4 and, thus, of the effector 3. In other words, a pivoting movement of the handle member 5 with respect to the tube shaft 2 causes a rotation of the crank member 8 connected to the handle member 1 by frictional engagement in the direction of rotation via the clutch 37. At the same time, however, the long-face pinion 26 is rotated along with the crank member 8 due to the fact that a kind of automatic lock by friction (efficiency of the gear) occurs by the mesh engagement between the actuating shaft 27 and the long-face pinion 26, said lock being possibly further assisted by slightly holding the actuating knob 6 and by the static friction between the actuating knob 6 and the handle member 5.

The rotation of the crank member 8 is transmitted via the crank or rather groove 10 at the front of the member 8 as well as the driving pin 11 into an axial movement of the pushing tube 12, which is transformed via the hinged rocking lever 19 into a pivoting movement of the instrument head 4 about the pivot axis thereof. However, this pivoting movement is automatically also performed by the output spur gear 21 which is fixed to the rotational axis of the effector 3 and is in mesh with the transmission spur gear 22. If, accordingly, the transmission spur gear 22 were stationary in this kind of operation, i.e. the pivoting operation, the pivoting movement of the instrument head 4 would cause the output spur gear 21 to roll off the transmission spur gear 22 in the same direction and, thus, would inevitably result in a superimposed motion of rotation of the effector 3.

As described in the foregoing, however, the long-face pinion 26 is rotated along with the crank member 8 during a pivoting movement of the handle member 5 and thus drives the drive shaft 24 inside the pushing tube 12. The transmission ratio between the long-face pinion 26 and the drive shaft 24 is calculated such that the transmission gear 22 is rotated by the drive shaft 24 about such an angle of rotation corresponding to the angle of rotation which is caused by the output gear 21 during a corresponding bending of the instrument head 4, whereby both rotations compensate each other due to their counter-rotation. In this constellation the relative position between the transmission spur gear 22 and the output spur gear 21 is maintained even during the bending motion of the instrument head 4 so that the effector 3 is held in each bending position of the instrument head 4 and during a bending motion, respectively, in its current position of rotation with respect to the instrument head 4.

As already stated in the foregoing, the clutch 37 in the present case provided in the form of a slipping clutch can only transmit a predetermined maximum torque. This maximum torque is selected such that it cannot be exceeded during normal use of the instrument. The maximum bending position as well as the maximum expanding position of the instrument head 4 is defined by a stop mechanism of the hinge between the instrument head 4 and the tube shaft 2, as described in the foregoing already. As soon as the instrument head 4 has reached these positions, a further bending of the instrument head 4 to the respective direction is no longer possible.

This constructional configuration can be advantageously used for an adjustment of the relative position of the handle member 5 to be predetermined with respect to the tube shaft 2, or rather for zero point adjustment as it is called. For this purpose, the instrument head 4 is bent in one or the other maximum stop position. After reaching the respective stop position the operator exerts an additional pivoting force upon the instrument handle 1 until the torque resulting herefrom exceeds the maximum torque of the clutch 37 to be transmitted. In this moment the connecting base 39 slides off inside the rotary shaft 8, whereby the original angle position of the instrument handle 1 relative to the tube shaft 2 changes for the selected maximum stop position of the instrument head 4.

In order to effect the operation of the effector 3, i.e. the function thereof, the lever 7 pivoted to the handle member 5 is provided in the present preferred embodiment. As already described in the foregoing concerning FIGS. 6a-6c, lever 7 is operatively connected via a reversing gear not shown in detail or an appropriate joint mechanism to the pushing rod 35 which is supported in the rotary shaft 24 and which axially reciprocates relative to the rotary shaft 24 upon a corresponding operation of the lever 7. A simple Bowden cable or deflecting lever would also be conceivable for a power transmission to the pushing rod 35.

FIG. 6a shows the relative position of the pushing rod 35 and the pushing pin 32 in a bending position of the instrument head 4 of 0° with the tongs being opened, FIG. 6b shows the relative position of the pushing rod 35 and the pushing pin 32 in a bending position of the instrument head 4 of approx. 45° with the tongs being opened, and FIG. 6c shows the relative position of the pushing rod 35 and the pushing pin 32 in a bending position of the instrument head 4 of approx. 45° with the tongs being closed.

As one can take from FIGS. 6a-6c, the pushing pin 32 is kept in constant contact with the beveled or chamfered distal front of the pushing rod 35 by the biasing force of the spring 33. When the pushing rod 35 is displaced in the direction of the instrument head 4 in the case of a 0° bending of the instrument head 4 according to FIG. 6a, the pushing pin 32 is displaced at the same speed and over the same distance as the pushing rod 35, i.e. without transmission, against the biasing force of the spring 33, whereby the jaw 30 of the tongs linked thereto is pivoted in the closing direction.

In this context, it is referred to the fact that by the displacing action of the pushing rod 35, the pushing pin 32, i.e. especially the center of the pin head radius, remains only approximately on the pivot axis of the instrument head 4, i.e. it moves in a kind of orbit during a bending motion of the instrument head 4. As already explained in the beginning of the description of figures, however, the regulating distances for opening and closing the tongs, for instance, are so small due to the set transmission rates that the orbit radius can be calculated theoretically, but it has no relevant influence on the position of the tongs for reasons of manufacture already (natural elasticity of the materials used, dimensional tolerances and play at the link joints and gear parts). In other words, the position of the tongs is determined by the position of the lever 7 which, in its turn, is held by an operator and thus is subjected, for instance, to non-controllable motions of the hand (trembling motions). Such disturbances produced due to manual operations are greater by far and, therefore, practically only relevant compared to the disturbances produced by the afore-described orbit motion.

That is to say, irrespective of the current position of the pushing rod 35 and the pushing pin 32, respectively, a bending of the instrument head 4 does generally not only cause the pushing pin 32 to pivot with respect to the pushing rod 35 but also causes the pin head 34 to slightly slide off the chamfered front of the pushing rod 35. By this little slide-off motion, the bearing contact of the pushing pin 32 with the front is maintained, wherein only such compensating longitudinal motion of the pushing pin 32 takes place as a result of its slide-off motion, however, which entails no practically relevant change of the closing or opening position at the effector 3. At the same time, however, some power deflection mechanism is provided so as to bring about a longitudinal motion of the pushing rod 35 into a longitudinal motion of the pushing pin 32 now provided at an angular position with respect to the pushing rod 35 by the beveling of the front of the pushing rod.

In other words, if the pushing rod 35 is displaced in a bending position>0° according to FIG. 6b in the closing direction of the effector 3, as illustrated in FIG. 6c, the chamfered front of the pushing rod 35 slides longitudinally past the pin head 34 and thus exerts an advance force on the pushing pin 32 which accordingly moves in the closing direction of the effector 3.

The invention claimed is:

1. A surgical instrument comprising a pivotable instrument handle connected to a tube shaft via a first pivotal engaging element at a proximal end of the surgical instrument, and, at a distal end of the surgical instrument, an instrument head linked so as to be bendable, the instrument head having an effector including a second pivotal engaging element that is rotatably supported,
    wherein said instrument handle has at least a turning knob and a handle lever for operating at least one selected from the group consisting of said instrument head and said effector via gear trains, the turning knob and the handle lever are located along the pivotable instrument handle, and the instrument handle, the turning knob and the handle lever are pivotable together with respect to the tube shaft at the first pivotal engaging element,
    wherein a clutch which permits an individual zero point adjustment at least over a predetermined pivoting range of said instrument handle is interposed in one of the gear trains effecting the bending motion of said instrument head, and
    wherein the zero point is a relative position of said instrument handle with respect to said tube shaft in which said instrument head adopts a predetermined bending position with respect to said tube shaft.

2. A surgical instrument according to claim 1, wherein the predetermined bending position is the maximum or minimum bending position of said instrument head.

3. A surgical instrument according to claim 1, wherein said clutch is a slipping clutch having a predetermined maximum transmittable torque.

4. A surgical instrument according to claim 2, wherein said clutch is a slipping clutch having a predetermined maximum transmittable torque.

5. A surgical instrument according to claim 2, wherein said clutch is arranged in a linking area between said instrument handle and said tube shaft.

6. A surgical instrument according to claim 3, wherein said clutch is arranged in a linking area between said instrument handle and said tube shaft.

7. A surgical instrument comprising a pivotable instrument handle connected to a tube shaft via a first pivotal engaging element at a proximal end of the surgical instrument, and, at a distal end of the surgical instrument, an instrument head linked so as to be bendable, the instrument head having an effector including a second pivotal engaging element that is rotatably supported,
    wherein said instrument handle has at least a turning knob and a handle lever for operating at least one selected from the group consisting of said instrument head and said effector via gear trains, the turning knob and the handle lever are located along the pivotable instrument handle, and the instrument handle, the turning knob and the handle lever are pivotable together with respect to the tube shaft at the first pivotal engaging element,
    wherein a clutch which permits an individual zero point adjustment at least over a predetermined pivoting range of said instrument handle is interposed in one of the gear trains effecting the bending motion of said instrument head,
    wherein the zero point is a relative position of said instrument handle with respect to said tube shaft in which said instrument head adopts a predetermined bending position with respect to said tube shaft, and said clutch being arranged in a linking area between said instrument handle and said tube shaft.

8. A surgical instrument comprising a pivotable instrument handle connected to a tube shaft via a first pivotal engaging element at a proximal end of the surgical instrument, and, at a distal end of the surgical instrument, an instrument head linked so as to be bendable, the instrument head having an effector including a second pivotal engaging element that is rotatably supported,
    wherein said instrument handle has at least a turning knob and a handle lever for operating at least one selected from the group consisting of said instrument head and said effector via gear trains, the turning knob and the handle lever are located along the pivotable instrument handle, and the instrument handle is pivotable with respect to the tube shaft at the first pivotal engaging element, wherein a clutch which permits an individual zero point adjustment at least over a predetermined pivoting range of said instrument handle is interposed in one of the gear trains effecting the bending motion of said instrument head, wherein the zero point is a relative position of said instrument handle with respect to said tube shaft in which said instrument head adopts a predetermined bending position with respect to said tube shaft, and wherein the turning knob is located at an opposite end along a longitudinal axis of the instrument handle from an end that is linked to the tube shaft.

9. A surgical instrument comprising a pivotable instrument handle connected to a tube shaft via a first pivotal engaging element at a proximal end of the surgical instrument, and, at a distal end of the surgical instrument, an instrument head linked so as to be bendable, the instrument head having an effector including a second pivotal engaging element that is rotatably supported, wherein said instrument handle has at least a turning knob and a handle lever for operating at least one selected from the group consisting of said instrument head and said effector via gear trains, the turning knob and the handle lever are located along the pivotable instrument handle, and the instrument handle is pivotable with respect to the tube shaft at the first pivotal engaging element, wherein a clutch which permits an individual zero point adjustment at least over a predetermined pivoting range of said instrument handle is interposed in one of the gear trains effecting the bending motion of said instrument head, wherein the zero point is a relative position of said instrument handle with respect to said tube shaft in which said instrument head adopts a predetermined bending position with respect to said tube shaft, and wherein when one of the turning knob and the handle lever rotates around an axis of the tube shaft, the other of the turning knob and the handle lever also rotates around the axis of the tube shaft.

* * * * *